United States Patent [19]

Feldl

[11] 4,020,482
[45] Apr. 26, 1977

[54] PATIENT MONITOR

[76] Inventor: Erich J. Feldl, 1516 Tenth St. Court, Manhattan, Kans. 66502

[22] Filed: Apr. 19, 1976

[21] Appl. No.: 678,460

[52] U.S. Cl. .............................. 340/279; 200/85 R; 340/272

[51] Int. Cl.² ........................................ G08B 21/00

[58] Field of Search .......... 340/279, 272, 278, 280; 200/85 R, 85 A, DIG. 35, 81 H, 81 R

[56] References Cited

UNITED STATES PATENTS

| | | | |
|---|---|---|---|
| 2,260,715 | 10/1941 | Ketchem | 200/85 R |
| 2,795,668 | 6/1957 | Puckett | 200/81 H |
| 2,818,477 | 12/1957 | Gollhofer | 340/279 |
| 3,533,095 | 10/1970 | Collins | 340/279 |
| 3,974,491 | 8/1974 | Sipe | 340/279 |

Primary Examiner—Glen R. Swann, III

[57] ABSTRACT

An elongated air inflated flexible bag is placed below the mattress of a hospital or nursing home bed and connected to a pressure actuated electrical switch signal at a remote attendant's station. The switch is a normally closed low pressure switch that remains open for as long as a patient's weight maintains an air pressure greater than the preset actuating pressure of the switch and closes when the patient's weight is removed and the pressure in the bag is thereby lowered, energizing a signal at the attendant's station.

1 Claim, 4 Drawing Figures

PATIENT MONITOR

BACKGROUND OF THE INVENTION

This invention relates generally to hospital alarm or monitoring systems. Its specific function is to signal and inform a nurse or attendant that a patient is preparing to get out of bed. It is a simple arrangement to prevent injuries that quite often occur when a lightly restrained patient manages to get free of the restraints and, not aware of a weakened physical or other condition, decides to get out of bed. This is of special concern with post operation patients and/or at night when other patients are asleep and the nursing staff is reduced.

SUMMARY OF THE INVENTION

The subject invention is novel in structure yet simple in design and is easily attached to a hospital or other bed. It is placed below the mattress between the mattress and the bed springs or other base and does not cause any adverse unevenness at the top of the mattress. It normally is located toward the head of the bed, in alignment with the upper torso of a patient, to cause actuation when the patient raises to a sitting position.

An elongated tube like flexible bag is approximately as long as the bed is wide, reaching from one side rail to the other, and is retained between two semi-flexible plates.

The plates are of thin plastic and are as long as the elongated bag and several times as wide as the bag is wide to present greater contact areas to mattress and bed thereby increasing air pressure inside the bag.

The pressure actuated electrical switch is mounted or retained by brackets to the wall close to the head of the bed and is connected to the air inflated bag by a small diameter flexible tube.

The pressure switch also has an electrical cord connecting it to the electrical signal or call system of the room when the room is so equipped or by conventional wiring system to a remote attendants station.

With the properly inflated air bag in place the weight of a patient causes the air pressure in the air bag to remain greater than the preset actuating pressure of the switch thus maintaining an open electrical circuit.

When the patient raises to a sitting position, removing the weight from the air bag area, the pressure in the air bag will decrease to below the preset actuating pressure of the switch thereby closing the electrical circuit and causing a light or buzzer alarm to be actuated.

The principle of my invention may be applied equally as well to different arrangements of the described components or their placement and location.

DETAILED DESCRIPTION OF THE DRAWINGS

Figure 1:
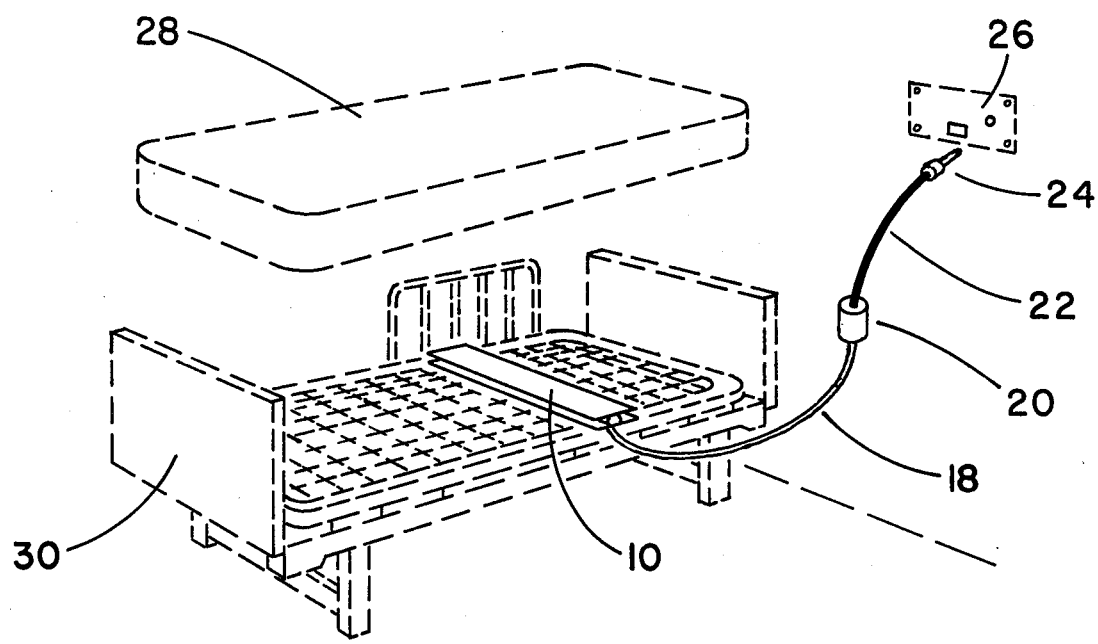
FIG. 1 is a perspective view of a hospital bed, partially exploded with the mattress separated from the bed to show the air bag and pressure plate assembly in place.

In FIG. 1 the air bag and pressure plate assembly is designated by general reference numeral 10. The total assembly includes an air hose 18, connecting the air bag to the pressure actuated electrical switch 20, an electrical cord 22 and an electrical connector 24 which connects the patient monitor system to the room call or alarm system. Wall panel 26 is meant to represent a typical room control panel. The mattress 28 is shown separated from the bed 30 to more clearly show the air bag assembly 10 in a typical location.

Figure 2:
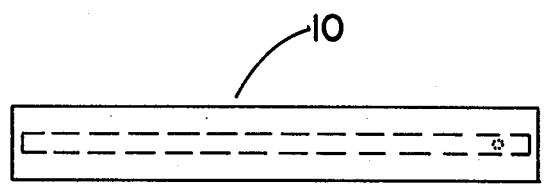
FIG. 2 is a top view of the assembly with the air bag location shown by interrupted lines.
Figure 3:
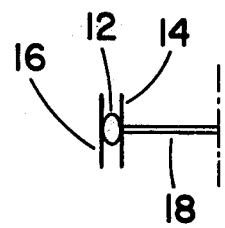
FIG. 3 is an end view of the assembly showing the air bag between the two pressure plates and part of the air hose connection.
Figure 4:
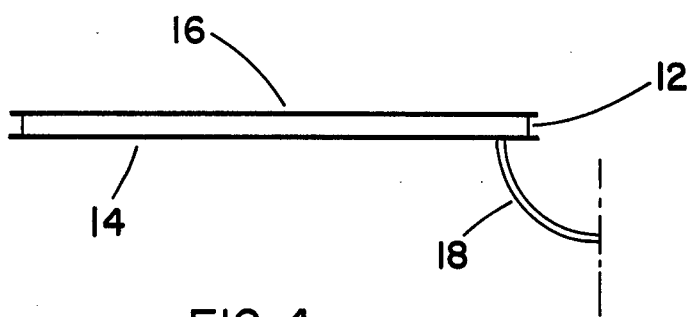
FIG. 4 is a side view of the assembly.

FIGS. 2, 3 and 4 are top, end and side views respectively of the air bag assembly 10. The elongated flexible air bag 12 is retained between two semi-flexible thin plates 14 and 16 and has an air hose 18 connected to it. When properly inflated and placed between the mattress 28 and the bed 30, the weight of a patient on the mattress 28 will cause the plates 14 and 16 to move closer to each other thereby compressing the air in the air bag 12. This air pressure causes the air pressure actuated electrical switch 20, which is connected to the air bag 12 by the air hose 18, to open its electrical contacts and maintain them in an open position. When the weight of the patient is removed from the area directly above the air bag assembly 10 the pressure in the air bag 12, air hose 18 and switch 20 is lowered to below a preset point, causing the electrical contact in the switch to close. With the switch 20 connected to a properly designed or modified room alarm system 26 the closing energizes a remotely located warning light or sound.

Changes may be made in the construction and arrangements of components without departing from the scope of the invention as defined in the following claims.

I claim:

1. A patient monitor alarm system that is placed below a bed patient and actuated by the weight of the patient so as to be sensitive to major changes in the patient's position to actuate a remote signal when said major changes occur, comprising:
    a flexible sealed enclosure which is filled with a fluid and placed under the patient,
    a pressure switch responsive to the pressure in said enclosure to close when the pressure is lowered below a preset level,
    a remote electrically operated signal that is energized by the closing of said switch, and
    wherein the weight of a patient compresses the fluid in the enclosure and raises its pressure above said preset level to hold the switch open, but removal of the patient's weight allows the switch to close, energizing the signal, further comprising:
    a pair of pressure plates between which the enclosure is located to give mechanical advantage to said weight by increasing the surface area sensing said weight and thereby raising the pressure in the enclosure.

* * * * *